US008425537B2

(12) United States Patent
Mitelberg et al.

(10) Patent No.: US 8,425,537 B2
(45) Date of Patent: Apr. 23, 2013

(54) METHOD OF USING INTERVENTIONAL MEDICAL DEVICE SYSTEM HAVING AN ELONGATION RETARDING PORTION

(75) Inventors: Vladimir Mitelberg, Austin, TX (US); John H. Thinnes, Jr., Miami Beach, FL (US); Keith Balgobin, Pembroke Pines, FL (US); William W. Sowers, Pembroke Pines, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

(21) Appl. No.: 13/608,532

(22) Filed: Sep. 10, 2012

(65) Prior Publication Data

US 2013/0006345 A1  Jan. 3, 2013

Related U.S. Application Data

(62) Division of application No. 11/461,231, filed on Jul. 31, 2006.

(51) Int. Cl.
*A61M 29/00* (2006.01)

(52) U.S. Cl.
USPC .................. 606/139; 606/200; 623/1.11

(58) Field of Classification Search .................. 606/108, 606/139, 153, 155, 191, 198, 200; 623/1.1, 623/1.11, 1.15, 1.16, 1.22; 600/585, 523; 604/28, 508, 523–525, 527; 464/78
See application file for complete search history.

(56) References Cited

U.S. PATENT DOCUMENTS

| 3,390,546 | A | * | 7/1968 | Jewell | 464/78 |
|---|---|---|---|---|---|
| 5,113,872 | A | * | 5/1992 | Jahrmarkt et al. | 600/585 |
| 5,147,317 | A | * | 9/1992 | Shank et al. | 604/164.13 |
| 5,171,262 | A | * | 12/1992 | MacGregor | 623/1.15 |
| 5,234,437 | A | * | 8/1993 | Sepetka | 606/108 |
| 5,250,071 | A | * | 10/1993 | Palermo | 606/198 |
| 5,282,478 | A | * | 2/1994 | Fleischhaker et al. | 600/585 |
| 5,304,131 | A | * | 4/1994 | Paskar | 604/95.04 |
| 5,312,415 | A | * | 5/1994 | Palermo | 606/108 |
| 5,330,491 | A | * | 7/1994 | Walker et al. | 606/148 |
| 5,378,236 | A | * | 1/1995 | Seifert | 604/99.04 |
| 5,405,338 | A | * | 4/1995 | Kranys | 604/524 |
| 5,421,348 | A | * | 6/1995 | Larnard | 600/585 |
| 5,499,995 | A | * | 3/1996 | Teirstein | 606/192 |
| 5,683,412 | A | * | 11/1997 | Scarfone | 606/205 |
| 5,725,549 | A | * | 3/1998 | Lam | 623/1.15 |
| 5,749,883 | A | * | 5/1998 | Halpern | 606/159 |
| 5,749,894 | A | * | 5/1998 | Engelson | 606/213 |
| 5,762,615 | A | * | 6/1998 | Weier | 600/585 |
| 5,800,455 | A | * | 9/1998 | Palermo et al. | 606/191 |

(Continued)

*Primary Examiner* — Corrine M McDermott
*Assistant Examiner* — Mark Mashack
(74) *Attorney, Agent, or Firm* — Cook Alex Ltd.

(57) ABSTRACT

Use of an interventional medical device system operable while within a body vessel is provided with a generally hollow tubular proximal portion, distal portion, and intermediate portion. The proximal portion and at least part of the distal portion remains outside of the body in use, with the remainder of the distal portion positioned within the body. The intermediate portion includes a spiral ribbon having adjacent turns, with at least one frangible bridge member between two adjacent turns. The proximal and distal portions are movable away from each other by elongating the spiral ribbon and, eventually, breaking the frangible bridge member. According to the method of using such a system to deploy an implantable medical device, such as an embolic coil, an actuation member is moved proximally with the proximal portion to disengage a bond or joint between the actuation member and the implantable medical device.

15 Claims, 2 Drawing Sheets

U.S. PATENT DOCUMENTS

| | | | |
|---|---|---|---|
| 5,891,128 A * | 4/1999 | Gia et al. | 606/1 |
| 6,036,670 A * | 3/2000 | Wijeratne et al. | 604/96.01 |
| 6,048,338 A * | 4/2000 | Larson et al. | 604/523 |
| 6,048,339 A * | 4/2000 | Zirps et al. | 604/525 |
| 6,102,932 A * | 8/2000 | Kurz | 606/200 |
| 6,126,685 A * | 10/2000 | Lenker et al. | 623/1.11 |
| 6,217,585 B1 * | 4/2001 | Houser et al. | 606/108 |
| 6,258,117 B1 * | 7/2001 | Camrud et al. | 623/1.16 |
| 6,277,126 B1 * | 8/2001 | Barry et al. | 606/108 |
| 6,287,318 B1 * | 9/2001 | Villar et al. | 606/191 |
| 6,344,041 B1 * | 2/2002 | Kupiecki et al. | 606/32 |
| 6,346,091 B1 * | 2/2002 | Jacobsen et al. | 604/57 |
| 6,350,278 B1 * | 2/2002 | Lenker et al. | 623/1.12 |
| 6,468,266 B1 * | 10/2002 | Bashiri et al. | 606/1 |
| 6,475,209 B1 * | 11/2002 | Larson et al. | 604/525 |
| 6,478,773 B1 * | 11/2002 | Gandhi et al. | 604/113 |
| 6,562,064 B1 * | 5/2003 | deBeer | 623/1.12 |
| 6,589,236 B2 * | 7/2003 | Wheelock et al. | 606/32 |
| 6,607,506 B2 * | 8/2003 | Kletschka | 604/96.01 |
| 6,835,185 B2 * | 12/2004 | Ramzipoor et al. | 604/57 |
| 7,115,183 B2 * | 10/2006 | Larson et al. | 156/293 |
| 7,192,440 B2 * | 3/2007 | Andreas et al. | 623/1.11 |
| 7,527,606 B2 * | 5/2009 | Oepen | 604/103.04 |
| 7,722,636 B2 * | 5/2010 | Farnan | 606/200 |
| 2003/0078649 A1 * | 4/2003 | Camrud et al. | 623/1.16 |
| 2003/0125711 A1 * | 7/2003 | Eidenschink et al. | 604/529 |
| 2003/0135266 A1 * | 7/2003 | Chew et al. | 623/1.16 |
| 2003/0208198 A1 * | 11/2003 | Hayzelden et al. | 606/41 |
| 2004/0034363 A1 * | 2/2004 | Wilson et al. | 606/108 |
| 2004/0199175 A1 * | 10/2004 | Jaeger et al. | 606/108 |
| 2005/0216018 A1 * | 9/2005 | Sennett | 606/79 |
| 2006/0069424 A1 * | 3/2006 | Acosta et al. | 623/1.12 |
| 2006/0100687 A1 * | 5/2006 | Fahey et al. | 623/1.11 |
| 2006/0149359 A1 * | 7/2006 | Richter et al. | 623/1.22 |
| 2007/0104752 A1 * | 5/2007 | Lee et al. | 424/422 |
| 2007/0123928 A1 * | 5/2007 | Farnan | 606/200 |
| 2007/0203519 A1 * | 8/2007 | Lorenzo et al. | 606/200 |
| 2007/0208405 A1 * | 9/2007 | Goodin et al. | 623/1.11 |
| 2008/0109057 A1 * | 5/2008 | Calabria et al. | 623/1.11 |

\* cited by examiner

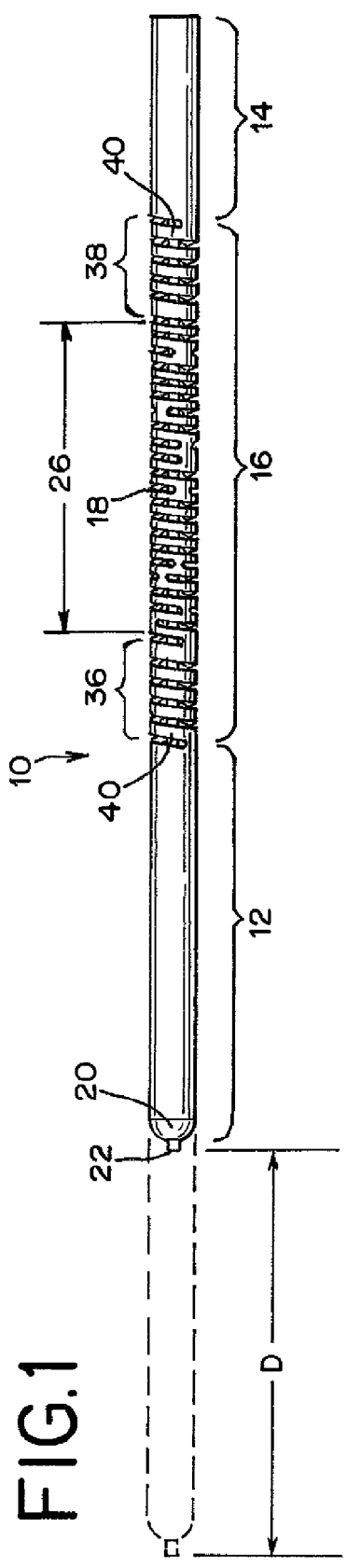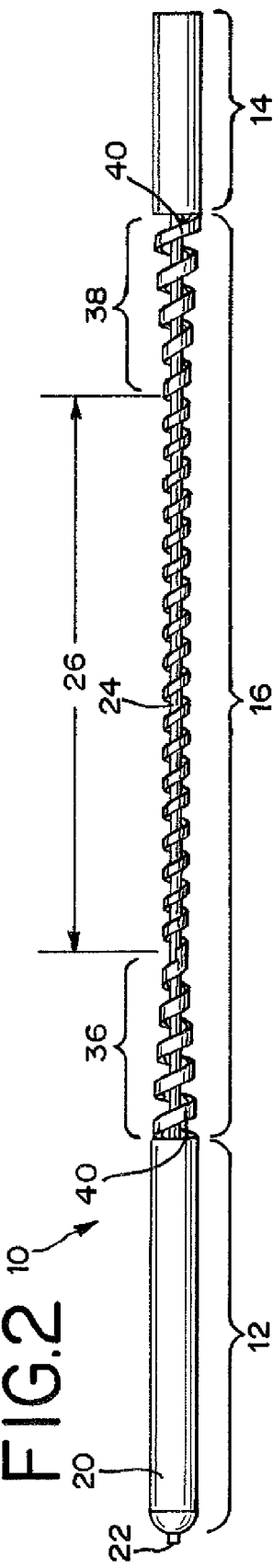

METHOD OF USING INTERVENTIONAL MEDICAL DEVICE SYSTEM HAVING AN ELONGATION RETARDING PORTION

This is a divisional of U.S. patent application Ser. No. 011/461,231, filed Jul. 31, 2006, hereby incorporated by reference hereinto.

FIELD OF THE INVENTION

This invention generally relates to interventional medical device systems that are navigable through body vessels of a human subject. More particularly, this invention relates to tubular devices having a frangible elongation retarding feature and methods of using the same.

DESCRIPTION OF RELATED ART

The use of catheter delivery systems for positioning and deploying therapeutic devices, such as dilation balloons, stents and embolic coils, in the vasculature of the human body has become a standard procedure for treating vascular diseases. It has been found that such devices are particularly useful in treating areas where traditional operational procedures are impossible or pose a great risk to the patient, for example in the treatment of intracranial aneurysms. Due to the delicate tissue surrounding intracranial blood vessels, especially for example brain tissue, it is very difficult and often risky to perform surgical procedures to treat defects of the intracranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to the accuracy of coil placement. For example, the coil detachment mechanism may cause the embolic coil to partially or fully dislodge from the predetermined site or dislodge previously deployed coils.

In response to accuracy concerns, numerous devices and release mechanisms have been developed in an attempt to provide a deployment system which allows control of the occlusion device after the device has been delivered by the catheter and to also provide a rapid release or detachment mechanism to release the device once it is in place. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that have the potential to interfere with other surgical and monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transforms the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body. This patent, and all other patents and references identified herein are hereby incorporated herein by reference.

Further, the above-identified delivery systems typically require electronic equipment powered by a power source. If the electronic equipment is defective or the power source fails, the procedure may be prolonged while the equipment is repaired or replaced. Prolonging the procedure may expose the patient to additional risk.

Even among delivery systems not requiring electronic equipment, a common feature is the need for a separate handle component, such as an attachable handle, a peelable sheath system, a syringe, that is manipulated by the medical professional to release the implantable device. Attachable handle components often require the use of additional components, such as a re-zip sheath, for proper operation including as an introducer component. This tends to increase the time and complexity of releasing the implantable device, as well as increasing the component and packaging costs.

Therefore, a need remains for a rapid release vascular occlusion deployment system or method that can function without electrical equipment or a power supply, does not develop chemical debris, is simple to manufacture, flexible and easy to guide through the vasculature of the body, provides excellent control over the occlusion device, and reduces the possibility of interference with other surgical and/or monitoring equipment. Further advantages could be realized with a handle system that has a low profile such as having the same outer diameter dimension as the overall delivery system.

SUMMARY OF THE INVENTION

In accordance with one embodiment or aspect of the present invention, an interventional medical device system operable while within a body vessel is provided with a generally hollow tubular proximal portion, distal portion, and intermediate portion. The proximal portion remains outside of the body in use, while at least a portion of the distal portion is positioned within the body during use. The intermediate portion, which typically remains outside of the body during use of the system, includes a spiral ribbon having adjacent turns, with at least one frangible bridge member between two adjacent turns. The proximal and distal portions are movable away from each other by elongating the spiral ribbon and, eventually, breaking the frangible bridge member.

According to another embodiment or aspect of the present invention, an interventional medical device system operable while within a body vessel is provided with a proximal portion handle, a distal portion, and an intermediate portion. At least a portion of the distal portion is positioned within the body during use. The intermediate portion includes a proximal helical section adjacent to the proximal handle portion, a distal helical section adjacent to the distal portion, and an intermediate helical section between the other two helical sections. The intermediate helical section includes a plurality of adjacent turns, with a frangible bridge member between two adjacent turns. The proximal and distal portions are movable away from each other by elongating the intermediate portion and, eventually, breaking the frangible bridge member.

To incorporate systems according to the preceding description into an implant delivery device, an actuation member is connected to the proximal portion, and an implantable medical device is associated with a deployment end of the actuation member. Movement of the proximal portion of the system away from the distal portion disengages the implantable device at a target location within the vasculature. The bridge member retards axial extension of the turns for improved control when releasing the implantable device.

According to yet another embodiment or aspect the present invention, a method of using an interventional medical device system in a body vessel includes providing a generally hollow tubular system. The tubular system includes a distal end portion, a proximal end handle portion, an intermediate portion, and an actuation member. The intermediate portion comprises a spiral having a plurality of turns and at least one bridge member between two adjacent turns. The actuation member is fixedly connected to the proximal end handle portion and extends to the distal end portion of the system. At least a portion of the distal end portion of the system is introduced into a body vessel and positioned generally adjacent to a target location within the vessel. The proximal end handle portion is then moved proximally with respect to the distal end portion, thereby breaking the bridge member and proximally moving the actuation member. If provided, an implantable medical device associated with a deployment end portion of the actuation member is released into the target location upon proximal movement of the actuation member.

Special application for the present invention has been found for tubular portions of embolic coil/implant detachment systems. However, the present invention is also applicable to tubular components of other devices adapted for movement through body lumens and requiring controlled elongation of the device, so it will be understood that the products and methods described herein are not limited to particular medical devices or particular surgical applications.

BRIEF DESCRIPTION OF THE DRAWINGS

FIG. 1 is a front elevational view of a medical device portion according to an aspect of the present invention, in a pre-actuation condition;

FIG. 2 is a front elevational view of the medical device portion of FIG. 1, in a post-actuation condition;

DESCRIPTION OF THE PREFERRED EMBODIMENTS

Figure 3:
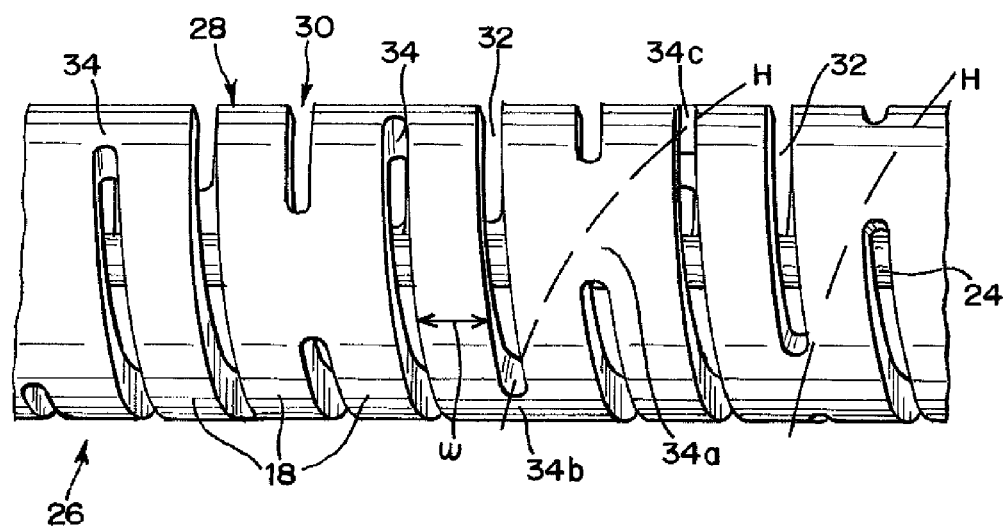
FIG. 3 is a detail view of an intermediate helical section of the medical device portion of FIG. 1.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIGS. 1 and 2 illustrate a generally hollow or tubular structure according to the present invention. When used herein, the terms "tubular" and "tube" are to be construed broadly and are not limited to a structure that is a right cylinder or strictly circumferential in cross-section or of a uniform cross-section throughout its length. For example, the tubular device or system is generally designated at 10 and shown as a substantially right cylindrical structure. However, the tubular system may have a tapered or curved outer surface without departing from the scope of the present invention. As an illustration and as described in greater detail herein, a proximal portion 12 of the system 10 may be used as a handle to manipulate the system 10, so it may be relatively large, tapered, and/or otherwise shaped for improved gripping without departing from the scope of the present invention.

The system 10 is comprised of a generally hollow tubular proximal portion or proximal portion handle or proximal end handle portion 12, distal portion or distal end portion 14, and intermediate portion 16. Preferably, the proximal and distal portions 12 and 14 are substantially non-compressible, non-elongatable metal hypotubes or portions of the same single hypotube. The intermediate portion 16 includes a plurality of spiral turns 18 and is elongatable, as illustrated in FIGS. 1 and 2. In a preferred embodiment, the system 10 is provided as an elongated metal hypotube, with the intermediate portion 16 comprising a spiral-cut portion thereof. The structure of the intermediate portion 16 is described in greater detail herein.

The proximal portion 12 remains outside of the body during use and may be used as a handle of the system 10 to be gripped and manipulated by a user. The proximal portion 12 may include a plug member 20 fixedly connected to an anchored end 22 of an elongated actuation member 24, which actuation member 24 extends at least from an interior lumen of the proximal portion 12 to an interior lumen of the distal portion 14. The actuation member 24 may be comprised of a metal or polymer and formed as a wire, tube, or other elongated structure. The anchored end 22 may be connected to the plug member 20 by any suitable means, including (but not limited to) adhesive, metallic bonding, and heat fusing. The function of the actuation member 24 is described in greater detail herein.

The distal portion 14 of the system 10 is adapted to be received by a body vessel. It will be appreciated that only a small section of the distal portion 14 is illustrated in FIGS. 1 and 2, as the distal portion 14 is preferably relatively lengthy with respect to the proximal portion 12, so that it can extend through the vasculature to reach a target location. For example, in one embodiment, the system 10 has a length in the range of approximately 180 and 200 cm, with the proximal portion 12 and the intermediate portion 16 collectively accounting for approximately 15 cm of the total length. Preferably, only a portion of the distal portion 14 is received within the body during use, with the remainder being positioned outside of the body to be manipulated by a user, as will be described in greater detail herein. If provided, the actuation member 24 extends into an interior lumen of the distal portion 14, with a deployment end (not illustrated) of the actuation member 24 adjacent to or extending beyond the end of the distal portion 14.

The proximal and distal portions 12 and 14 are separated by the intermediate portion 16, which preferably remains outside of the body during use. Sections of a preferred intermediate portion 16 are shown in greater detail in FIGS. 3 and 4. The intermediate portion 16 includes at least an interrupted spiral section 26 (FIG. 3), also referred to herein as an intermediate helical section. The intermediate helical section 26 comprises a spiral ribbon 28 having adjacent turns 18, similar to a typical wound wire or spiral-cut tube. However, while the turns of a typical wound wire or spiral-cut tube are defined and separated by a continuous helical opening, the turns 18 of the intermediate helical section 26 are separated by an interrupted spiral 30. The interrupted spiral is characterized by an open or cut section 32 and at least one uncut section or frangible bridge member 34 between two adjacent turns 18. Preferably, the intermediate helical section 26 includes a plurality of alternating cut and uncut sections 32 and 34. The alternating cut and uncut sections 32 and 34 preferably define a single substantially helical pattern, which may simplify manufacture of the intermediate helical section 26.

Each bridge member 34 may be formed according to the teachings of an application entitled "Interventional Medical Device Component Having An Interrupted Spiral Section And Method Of Making The Same" (Ser. No. 11/461,219), filed herewith on Jul. 31, 2006, which is hereby incorporated herein by reference. This application also provides details of bridge member distribution that may be suitable for some embodiments of the present disclosure. Briefly, the intermediate helical section 26 may be formed by spiral-cutting a portion of a hypotube. The cutting member is deactivated at selected intervals, while still moving in a helical path with respect to the hypotube, in order to create frangible bridge members 34. Alternatively, the intermediate helical section 26 may be provided as a wound wire, with welds between adjacent turns of the wire serving as frangible bridge members 34. In the present disclosure, the bridge members typically are designed to be frangible as discussed herein. Other methods of manufacturing the intermediate helical section 26 may also be practiced without departing from the scope of the present invention.

Preferably, each frangible bridge member is out of axial alignment with any and each frangible bridge member immediately adjacent thereto. For example, FIG. 3 illustrates an exemplary bridge member 34a out of axial alignment with the adjacent bridge members 34b, 34c. Rather than being axially aligned, the bridge members 34 of FIG. 3 are arranged in a generally helical pattern "H", which provides an advantageous distribution that promotes substantially uniform performance characteristics (e.g., flexibility, rigidity, and stretch resistance) along the intermediate helical section 26. A regular, non-axially aligned distribution may also be preferred to prevent preferential bending of the intermediate helical section 26 before or after the frangible bridge members 34 are broken.

The intermediate portion 16 is axially elongatable from a pre-actuation condition (FIG. 1) to a post-actuation condition (FIG. 2) by proximally moving the proximal portion 16 away from the distal portion 14. The total elongation length is represented in FIG. 1 at "D". The presence of the frangible bridge members 34 makes the system 10 more stretch resistant than a typical wound ribbon or spiral cut tube, so the elongation of the intermediate portion 16 is more controlled.

Each frangible bridge member 34 preferably is adapted to break after the turns 18 of the intermediate helical section 26 begin to elongate, but before the post-actuation condition of FIG. 2. As an elongatable structure, the intermediate helical section 26 will begin to elongate, at least nominally, when subjected to any longitudinally directed tensile force, but the frangible bridge members 34 may be adapted to break at a greater threshold pull force. For example, in neurovascular applications, the frangible bridges may be adapted to break at a pull force in the range of approximately 0.2 and 0.6 lbf, preferably at a pull force of approximately 0.4 lbf. Of course, other threshold pull forces may be used, and may even be preferred for applications outside of the neurovasculature.

Preferably, the minimum breaking force is greater than the force required to withdraw the system 10 from the vasculature; otherwise the bridge member or members 34 may break during repositioning or removal of the system. The required breaking force of the bridge member 34 is determined by a number of factors and can be calibrated to break at a preselected pull force by adjusting the number, width, thickness, arcuate extent, and/or constituent material of the bridge members 34. Furthermore, when a plurality of bridge members 34 are provided, they need not be identical, but can be differently configured from each other to allow, for example, breaking and elongation at different pull forces and in stages.

Figure 4:
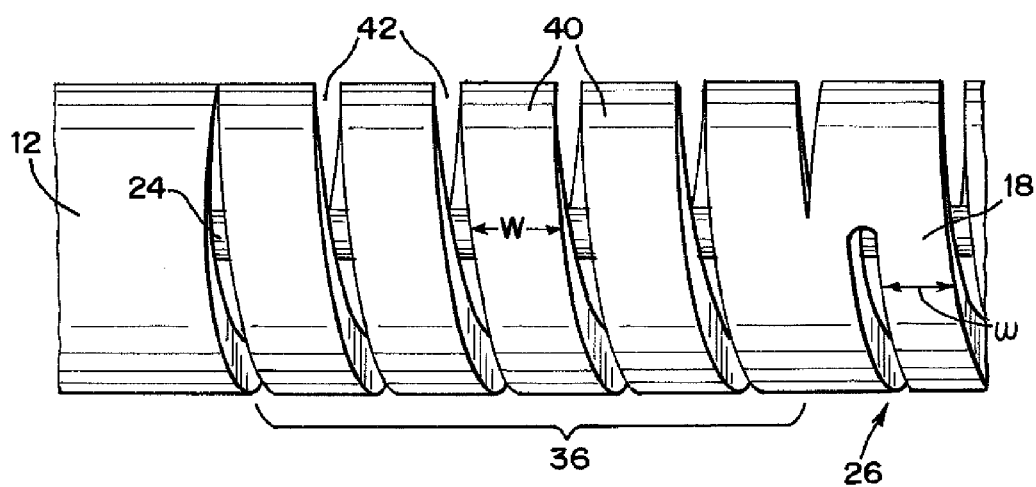
FIG. 4 is a detail view of a proximal helical section of the medical device portion of FIG. 1.

In the embodiment of FIGS. 1 and 2, the intermediate helical section 26 is bracketed by a proximal helical section 36 and a distal helical section 38. The illustrated proximal helical section 36 is shown in greater detail in FIG. 4, with the distal helical section 38 preferably being a mirror image thereof. As shown in FIG. 4, the proximal and distal helical sections 36 and 38 are preferably comprised of a plurality of turns 40 of a typical wound wire or spiral-cut tube, the turns 40 being defined and separated by a continuous helical opening 42. If one or both are provided, the proximal and distal helical sections 36 and 38 each act as a transition or buffer between the interrupted spiral section 26 and the proximal and distal portions 12 and 14 of the system 10. If the interrupted spiral 30 is positioned adjacent to the substantially tubular proximal and/or distal portions 12 and 14, then there is a risk that large stress concentrations can develop at the interfaces between the intermediate helical section 26 and the uncut proximal and distal portions 12 and 14, which may lead to fracture of the system 10 at the interfaces. The presence of the proximal and/or distal helical sections 36 and 38 reduces this risk.

The width of an exemplary turn of the proximal helical section 36 is designated in FIG. 4 as "W", while the width of an exemplary turn of the intermediate helical section 26 is designated in FIGS. 3 and 4 as "ω". In a preferred embodiment, the width "W" of at least one turn 40 of one of the proximal and distal helical sections 36 and 38 is greater than the width "ω" of at least one turn 18 of the intermediate helical section 26. This provides a smoother transition between the intermediate helical section 26 and the proximal and/or distal portions 12 and 14 of the system 10, compared to a configuration wherein the turns 40 of the proximal and distal helical sections 36 and 38 have an equal or smaller width than the turns 18 of the intermediate helical section 26. In a preferred embodiment, the turns 40 of the proximal and distal helical sections 36 and 38 are substantially identical to each other, the turns 18 of the intermediate helical section 26 are identical to each other, and the width "W" of the turns 40 of the proximal and distal helical sections 36 and 38 is greater than the width "ω" of the turns 18 of the intermediate helical section 26.

It is further contemplated that, instead of or in addition to providing the turns 40 of the proximal and distal helical sections 36 and 38 with increased widths W, the turns 40 may be provided with frangible or non-frangible bridge members (not illustrated) between adjacent turns 40. In particular, an interrupted spiral according to the foregoing description is created, with the bridge members of the proximal and distal helical sections 36 and 38 being wider and stronger than the frangible bridge members 34 of the intermediate helical section 26, such that they do not break during normal use or only break after the frangible bridge members 34 of the intermediate helical section 26. As with the frangible bridge members 34 of the intermediate helical section 26, it may be preferred for bridge members of the proximal and/or distal helical sections to be arranged in a regular, non axially aligned distribution to avoid creating a bending preference.

Special application for systems according to the present invention has been found in delivery devices for releasing implantable medical devices, such as embolic coils, to a target location of a body vessel. For such devices, an implant is operatively connected to a deployment end of the actuation member 24. The implant is initially positioned adjacent to the end of the distal end portion 14 of the system 10, and connected and oriented such that proximal movement of the actuation member 24 with respect to the distal end portion 14 will release the implant. This may be accomplished in any of a number of ways, such as by positioning the implant in abutment with the end of the distal end portion 14, in which case proximal relative movement of the actuation member 24 will cause the implant to bear against the distal end portion 14, thereby disengaging a connection such as a bond or joint between the actuation member 24 and the implant and releasing the implant.

In use, part of the distal end portion 14 of the system 10 is inserted into a body vessel in the pre-actuation condition of FIG. 1. If preferred, the distal end portion 14 may be delivered in a separate introducer or catheter, or can be fed through a catheter already placed within the vessel. The distal end portion 14 is positioned adjacent to a target location of the body vessel and held in place. The proximal end handle portion 12 and the intermediate portion 16 remain outside of the body, along with part of the distal end portion 14. The proximal end handle portion 12 is moved proximally with respect to the distal end portion 14, causing the intermediate portion 16 to begin to elongate by stretching the turns 18. Thereafter, the intermediate portion 16 continues to elongate by either stretching the turns 40 (if provided) or breaking a frangible bridge member 34, the order of elongation depending on the relative strengths of the frangible bridge member or members 34 and (if provided) the turns 40 of the proximal and distal helical sections 36 and 38.

Elongating the intermediate portion 16 thusly also causes the actuation member 24, which is fixed to the proximal end handle portion 12, to move proximally. Eventually, when sufficient pull force has been applied to the proximal end handle portion 12, the frangible bridge members 34 will break and the intermediate portion 16 will elongate into the post-actuation condition of FIG. 2. If the proximal and distal helical sections 36 and 38 are also provided with frangible bridge members, then sufficient force must be provided to break all of the bridge members of the intermediate section 16 before the system 10 achieves the post-actuation condition. In the post-actuation condition, the actuation member 24 has been moved proximally to such a degree that the implant (not shown) is released from the deployment end into the target location of the body vessel. Deployment end and implant details for a particular embodiment suitable for use with the present handle arrangement are found in an application entitled "Implantable Medical Device Detachment System and Methods of Using the Same" (Ser. No. 11/461,245), filed herewith on Jul. 31, 2006, which is hereby incorporated herein by reference.

By a preferred safety mechanism, the system 10 may be adapted such that the actuation member 24 will not release the implantable medical device until the frangible bridge members 34 break. This may be achieved, for example, by preventing release of the implant until a pre-selected actuation member displacement "D" (FIG. 1) that can only be achieved when the frangible bridge members 34 have been broken. At a pull force below the breaking force, the actuation member 24 is only partially retracted, so the implant remains connected to the actuation member 24 and the system 10 may be repositioned before deploying the implant.

It will be seen from the preceding description that delivery devices incorporating systems according to the present invention eliminate numerous problems associated with known devices. In particular, no power source is required to release the implant, so the system is less vulnerable to power outages. Furthermore, a separate handle member is not required, because one is inherent in the system, which decreases costs, complexity, and the time needed to release an implant.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A method of using an interventional medical device system in a body vessel, comprising:
    providing a generally hollow tubular system comprising:
        (a) a distal end portion, (b) a proximal end handle portion, (c) an intermediate portion between the distal end portion and the proximal end handle portion, said intermediate portion comprising a spiral having a plurality of turns and at least one bridge member between two adjacent turns, and (d) an actuation member fixedly connected to the proximal end handle portion and extending generally from an interior of the proximal end handle portion of the system to an interior of the distal end portion of the system;
    introducing a portion of the distal end portion of the system into a body vessel;
    positioning the distal end portion of the system generally adjacent to a target location within the body vessel;
    moving the proximal end handle portion proximally with respect to the distal end portion; and
    thereby breaking the bridge member and proximally moving the actuation member.

2. The method of claim 1, wherein said moving of the proximal end handle portion, said breaking of the bridge member, and said proximal moving of the actuation member comprise the same proximal movement of the proximal end handle portion of the system.

3. The method of claim 1, wherein said providing of a generally hollow tubular delivery system includes providing an intermediate portion comprising a plurality of the bridge members, and wherein said breaking the bridge member includes breaking said plurality of bridge members.

4. The method of claim 1, wherein said providing of a generally hollow tubular delivery system includes providing the intermediate portion with a proximal helical section adjacent to the proximal end handle portion, a distal helical section adjacent to the distal end portion of the system, and an intermediate helical section substantially defined by the intermediate helical section turns and the bridge member, and wherein said moving of the proximal end handle portion includes elongating the proximal helical section and the distal helical section.

5. The method of claim 1, further including providing an implantable medical device and operatively connecting same to a deployment end portion of the actuation member, wherein said moving of the proximal end handle portion which proximally moves the actuation member also disengages the implantable medical device from the actuation member and delivers the implantable medical device for implanting same within the body vessel.

6. The method of claim 1, wherein said providing of a generally hollow tubular delivery system includes providing the intermediate portion with (a) a proximal helical section adjacent to the proximal end handle portion and defined by a plurality of turns, (b) a distal helical section adjacent to the distal end portion of the system and defined by a plurality of turns, (c) an intermediate helical section substantially defined by the intermediate helical section turns and the bridge member, and (d) at least one bridge member between two adjacent turns of one of the proximal helical section and the distal helical section and adapted to break after the bridge member of the intermediate helical section; and wherein said moving of the proximal end handle portion includes breaking the bridge member of the proximal helical section or the distal helical section.

7. A method of using an interventional medical device system in a body vessel, comprising:
 providing a generally hollow tubular system comprising:
  (a) a distal end portion, (b) a proximal end handle portion, (c) an intermediate portion between the distal end portion and the proximal end handle portion, said intermediate portion comprising a spiral-cut section of a hypotube having a plurality of turns and with an interrupted spiral-cut section having a plurality of frangible bridge members between two adjacent turns, and (d) an actuation member fixedly connected to the proximal end handle portion and extending generally from an interior of the proximal end handle portion of the system to an interior of the distal end portion of the system;
 said providing further including providing bridge members out of axial alignment with a bridge member immediately adjacent thereto;
 introducing a portion of the distal end portion of the system into a body vessel;
 positioning the distal end portion of the system generally adjacent to a target location within the body vessel;
 moving the proximal end handle portion proximally with respect to the distal end portion; and
 thereby breaking bridge members and proximally moving the actuation member, and the bridge members retard axial extension of the spiral ribbon thereat in response to application of a force applied to the intermediate portion from the proximal portion.

8. The method of claim 7, wherein said moving of the proximal end handle portion, said breaking of the bridge member, and said proximal moving of the actuation member comprise the same proximal movement of the proximal end handle portion of the system.

9. The method of claim 7, wherein said breaking the bridge member includes breaking said plurality of bridge members.

10. The method of claim 7, wherein said providing of a generally hollow tubular delivery system includes providing the intermediate portion with a proximal helical section adjacent to the proximal end handle portion, a distal helical section adjacent to the distal end portion of the system, and an intermediate helical section substantially defined by the intermediate helical section turns and by the bridge members, and wherein said moving of the proximal end handle portion includes elongating the proximal helical section and the distal helical section.

11. The method of claim 7, further including providing an implantable medical device and operatively connecting same to a deployment end portion of the actuation member, wherein said moving of the proximal end handle portion which proximally moves the actuation member also disengages the implantable medical device from the actuation member and delivers the implantable medical device for implanting same within the body vessel.

12. The method of claim 7, wherein said providing of a generally hollow tubular delivery system includes providing the intermediate portion with (a) a proximal helical section adjacent to the proximal end handle portion and defined by a plurality of turns, (b) a distal helical section adjacent to the distal end portion of the system and defined by a plurality of turns, (c) an intermediate helical section substantially defined by the intermediate helical section turns and the bridge members, and (d) the breaking includes breaking at least one bridge member between two adjacent turns of one of the proximal helical section and the distal helical section after breaking the bridge member of the intermediate helical section; and wherein said moving of the proximal end handle portion includes breaking the bridge member of the proximal helical section or the distal helical section.

13. The method of claim 7, further including fixedly connecting the actuation member to the proximal end handle and extending same through a passageway of the proximal end handle and through a passageway of the distal end portion.

14. The method of claim 13, further including deploying an implantable medical device by movement of the activation member at a location distal of the intermediate portion when the spiral ribbon axially elongates between the proximal and distal portions.

15. The method of claim 7, wherein said breaking occurs at a pre-selected pull force.

* * * * *